US007683103B2

(12) United States Patent
Sawada et al.

(10) Patent No.: US 7,683,103 B2
(45) Date of Patent: Mar. 23, 2010

(54) DENTAL POLYMERIZABLE COMPOSITION

(75) Inventors: Hideo Sawada, Hirosaki (JP); Junji Tagami, Bunkyo-ku (JP); Toru Nikaido, Bunkyo-ku (JP); Khairul Matin, Bunkyo-ku (JP); Yoshinori Kadoma, Bunkyo-ku (JP); Eiichi Masuhara, Chiyoda-ku (JP); Koichi Okada, Kurashiki (JP); Junichi Yamauchi, Kurashiki (JP)

(73) Assignee: Kuraray Medical Inc., Kurashiki-shi (JP)

( * ) Notice: Subject to any disclaimer, the term of this patent is extended or adjusted under 35 U.S.C. 154(b) by 138 days.

(21) Appl. No.: 11/659,811

(22) PCT Filed: Aug. 11, 2005

(86) PCT No.: PCT/JP2005/014744

§ 371 (c)(1),
(2), (4) Date: Oct. 12, 2007

(87) PCT Pub. No.: WO2006/016649

PCT Pub. Date: Feb. 16, 2006

(65) Prior Publication Data

US 2008/0039592 A1 Feb. 14, 2008

(30) Foreign Application Priority Data

Aug. 11, 2004 (JP) .............................. 2004-234622

(51) Int. Cl.
*A61K 6/00* (2006.01)
(52) U.S. Cl. ........................ 522/121; 522/182; 522/178; 523/116; 523/118; 433/217.1; 433/228.1
(58) Field of Classification Search ................ 525/305, 525/416; 523/113, 115, 116, 118; 433/217.3, 433/217.1, 228.1; 522/156, 121, 182, 178, 522/181
See application file for complete search history.

(56) References Cited

U.S. PATENT DOCUMENTS

| 4,684,705 | A | * | 8/1987 | Yamamoto et al. .......... 526/246 |
| 4,990,582 | A | * | 2/1991 | Salamone ................... 526/245 |
| 5,026,902 | A |   | 6/1991 | Fock et al. |
| 5,324,803 | A | * | 6/1994 | Sawada et al. .............. 526/279 |
| 6,110,640 | A | * | 8/2000 | Kawamura et al. ....... 430/270.1 |
| 6,184,339 | B1 | * | 2/2001 | Stansbury et al. ........... 528/407 |
| 6,274,060 | B1 | * | 8/2001 | Sakashita et al. ........... 252/8.62 |
| 6,887,920 | B2 | * | 5/2005 | Ohtsuki et al. .............. 523/116 |

FOREIGN PATENT DOCUMENTS

| JP | 60-42411 | | 3/1985 |
| JP | 5-155730 | | 6/1993 |
| JP | 5-255032 | | 10/1993 |
| JP | 05-255032 | * | 10/1993 |
| JP | 6-172456 | | 6/1994 |
| JP | 10-7731 | | 1/1998 |
| JP | 10-245419 | * | 9/1998 |
| JP | 10-251348 | | 9/1998 |
| JP | 10-510531 | | 10/1998 |
| JP | 2000-312689 | | 11/2000 |
| JP | 2003-48842 | | 2/2003 |
| JP | 2003-95838 | | 4/2003 |
| JP | 2003-253022 | | 9/2003 |

OTHER PUBLICATIONS

Sawada, Hideo; Fluorinated Peroxides, Chemical Reviews, 1996, 96, 1779-1808.*

* cited by examiner

*Primary Examiner*—Susan W Berman
(74) *Attorney, Agent, or Firm*—Oblon, Spivak, McClelland, Maier & Neustadt, L.L.P.

(57) ABSTRACT

A dental polymerizable composition comprising (a) a fluorine compound comprising a chain polymer having a main chain comprising a monomer unit having a hydrophilic group, and terminal groups comprising a fluoroalkyl group at each of both ends of the main chain; (b) a polymerizable monomer; and (c) a polymerization initiator. The dental polymerizable composition can be suitably used, for example, for dental composite resins, such as dental composite filler materials, crowning materials, and bonding materials; dental adhesive agents, such as teeth-straightening adhesive agents, cavity-coating adhesive agents, and tooth fissure sealing materials; denture base materials, denture base mucosal adjusting materials, fissure sealants, coating agents applied to tooth surface or dental prosthetic, surface glazes, and the like, and especially for various coating applications, for example, a fissure sealant, a coating agent to tooth surface or dental prosthetic, surface stains or a surface glaze, a hypersensitive inhibitor, a dental manicure, or the like.

10 Claims, No Drawings

DENTAL POLYMERIZABLE COMPOSITION

This application is a 371 of PCT/JP05/14744 filed Aug. 11, 2005.

TECHNICAL FIELD

The present invention relates to a dental polymerizable composition. More specifically, the present invention relates to a dental polymerizable composition which can be suitably used for various filler materials, a mending material, a denture base material, a crowning material, a bonding material, an adhesive agent, a coating agent, a dental plaque-forming inhibitor, a hypersensitive inhibitor, and the like, each in the field of dental materials.

BACKGROUND ART

A dental polymerizable composition composed of a polymerizable monomer and a polymerization initiator has been widely clinically used at present. The dental polymerizable composition has been used, for example, in a dental restorative material which is so-called a composite resin usable in filling or repairing fracture of teeth or cavities of dental caries, a dental adhesive agent for adhering a crowning prosthetic such as a composite resin or inlay and crown to teeth, or cement, further artificial teeth or a denture base material, a coating agent, or the like.

However, when these resin-based restorative materials are present in the oral cavity for a long period of time, it has been pointed out that discoloration or coloration is generated on its surface, and plaque is likely to be deposited thereon. Also, when plaque is deposited on surfaces of natural teeth, without being limited to the restorative material, it is said to be causes of various oral cavity diseases such as dental caries or periodontal diseases.

In recent years, it has been tried to inhibit the deposition of the plaque by giving the surface of teeth or a restorative material anti-staining property, and a dental plaque-forming inhibitor comprising a polymer containing a monomer unit containing a phosphoric acid group and a monomer unit containing an oxyethylene group in the main chain has been proposed (see, for example, Patent Publication 1).

In addition, in order to inhibit the discoloration or coloration of the surface of the resin-based dental restorative material or the accumulation of the plaque, dental materials in which a fluorine-based material is applied, such as a coating agent comprising a silicone oligomer containing fluoroalkyl groups on both ends of the main chain as an active ingredient (see, for example, Patent Publication 2); a relining material for removable denture or a coating composition each containing a fluorine-containing (meth)acrylate as a part of the monomer (see, for example, Patent Publications 3 to 4); and a coating composition comprising a fluorine-containing polymer obtained by copolymerizing a monomer having a polar group such as acrylic acid with a monomer containing a fluorine atom (see, for example, Patent Publication 5) have been proposed.

Further, as an attempt of applying a fluorine compound to dental material applications for the purpose other than the anti-staining property, a glass ionomer cement curing liquid containing a poly(meth)acrylic acid having a fluoroalkyl group at both ends of the main chain has been proposed (see, for example, Patent Publication 6). In addition, when the scope is broadened to applications other than the dental materials, as techniques of imparting a base material with an anti-staining property, a technique of applying a polymer having a fluoroalkyl group on both ends of the main chain, the main chain being constituted by monomer units having a phosphoric acid group or an N,N-di-substituted aminocarbonyl group, as a surface-treating agent to fibers, metals, plastics, papers, and the like (see, for example, Patent Publications 7 to 9); a technique of applying a photopolymerizable coating agent composition comprising a polymer having a fluoroalkyl group on both ends of the main chain, and a photopolymerizable monomer or a prepolymer in the surface modification of plastics, wood materials, fibers, metals, and the like (see, for example, Patent Publication 10); and the like have been proposed.

Patent Publication 1: Japanese Patent Laid-Open No. 2003-48842
Patent Publication 2: Japanese Patent Laid-Open No. Hei 5-155730
Patent Publication 3: Japanese Patent Laid-Open No. 2000-312689
Patent Publication 4: Japanese Patent Laid-Open No. 2003-95838
Patent Publication 5: Japanese Unexamined Patent Publication No. Hei 10-510531
Patent Publication 6: Japanese Patent Laid-Open No. Hei 5-255032
Patent Publication 7: Japanese Patent Laid-Open No. Hei 10-7731
Patent Publication 8: Japanese Patent Laid-Open No. Hei 10-251348
Patent Publication 9: Japanese Patent Laid-Open No. 2003-253022
Patent Publication 10: Japanese Patent Laid-Open No. Hei 10-245419

DISCLOSURE OF INVENTION

Problems to be Solved by the Invention

However, since the dental plaque-forming inhibitor described in Patent Publication 1 cannot be retained on the surfaces of teeth or a restorative material in the oral cavity for a long time, there is a disadvantage that the dental plaque-forming inhibitor is poor in sustainability of the effects, thereby lacking its practicality.

The coating agent described in Patent Publication 2 has a disadvantage that the coating agent is poor in sustainability of anti-staining property because the fluorine compound (silicon oligomer) is easily peeled off from a base material surface when subjected to abrasion with a toothbrush, or the like, and also has a disadvantage that since the hydrophobicity of the fluorine compound is generally too strong, it is very difficult to peel off stains such as oils and tobacco stains that are deposited thereon.

In the denture base back coating material and the coating composition described in Patent Publications 3 and 4, a (meth)acrylate in which an alcohol residue is a fluoroalkyl group is used as a fluorine compound (fluorine-containing (meth)acrylate). However, remarkable effects cannot be obtained unless the (meth)acrylate having such a structure has to be blended in a given ratio or more (usually 50% or more) in the relining material for removable denture or the coating composition, thereby making it disadvantageous in costs.

Also, Patent Publication 5 describes that the polymerizable composition comprising a fluorine-containing polymer and a monomer inhibits the deposition of the dental plaque. The fluorine-containing polymer that is concretely described therein is only a random copolymer composed of a fluorine-containing monomer and a polar group-containing monomer, so that a high anti-staining effect has not been found as far as studies made by the present inventors.

Since the dental composition described in Patent Publication 6 differs from a polymerizable composition in that the dental composition is a cement composition formed by ionic cross-linking. Therefore, the dental composition has a disadvantage that the dental composition cannot be used in applications that would be exposed to the surface of teeth or the restorative material.

The techniques described in Patent Publications 7 to 9 are techniques of increasing the anti-staining property of a base material by adsorbing a fluorine compound (polymer) having excellent anti-staining property to a substrate material of fibers, papers, plastics, metals, and the like. However, since the fluorine compound is easily peeled off from the surface of the substrate material in the same manner as in Patent Publication 2, the techniques have a disadvantage that the anti-staining property is not sustained, and the techniques do not suggest the combined use of a fluorine compound and a polymerizable monomer.

The photopolymerizable coating agent described in Patent Publication 10 is purposed for the surface modification of general industrial manufactured articles, and these industrial manufactured articles do not give suggestions regarding their use as a coating agent for natural teeth or a dental restorative material which has completely different environment during the application and after the application. In other words, in dental applications, not only simple anti-staining is required, but other physical properties are also required. This is because it is as a matter of course required, for example, in a tooth surface coating agent or a dental composite to exhibit as basic properties discoloration or coloration or abrasion resistance in the oral cavity, anti-discoloration property of the cured product itself, property of preventing accumulation of plaques or biofilms, and adhesive durability with the tooth surface.

Therefore, a dental polymerizable composition useful as a coating agent or a dental composite resin, the dental polymerizable composition being capable of giving the surface the anti-staining property and the plaque-adhesion inhibition with a convenient method, and having excellent abrasion resistance of a cured product, anti-discoloration and adhesion with the tooth surface, has been desired.

An object of the present invention is to provide a dental polymerizable composition having excellent anti-staining property of the surface of the cured product, plaque-adhesion inhibition, abrasive resistance, anti-discoloration of the cured product itself, aesthetic appreciation, and adhesion with the tooth surface, in oral cavity.

Means to Solve the Problems

The present invention relates to:
(1) a dental polymerizable composition comprising:
(a) a fluorine compound comprising a chain polymer having a main chain comprising a monomer unit having a hydrophilic group, and terminal groups comprising a fluoroalkyl group at each of both ends of the main chain [hereinafter referred to as fluorine compound (a)];
(b) a polymerizable monomer [hereinafter referred to as polymerizable monomer (b)]; and
(c) a polymerization initiator [hereinafter referred to as polymerization initiator (c)];
(2) the dental polymerizable composition as defined above, further comprising (d) a solvent;
(3) a single-liquid dental coating agent comprising the dental polymerizable composition as defined above in a single wrapping; and
(4) a method for curing a dental polymerizable composition, characterized in that the method comprises applying the dental polymerizable composition as defined above to surfaces of teeth or a dental restorative material, allowing a solvent contained in the dental polymerizable composition to evaporate, and curing the residue, thereby forming a layer comprising a fluorine compound on the surfaces of the teeth or the dental restorative material.

Effects of the Invention

The surface of the cured product obtained by polymerizing the polymerizable composition of the present invention exhibits excellent anti-staining property that the surface is less likely to be deposited with stains derived from water-repellent and oil-repellent properties of fluorine, as well as oil-based stains are less likely to be deposited because of having a hydrophilic group. In addition, the surface of this cured product is hardly likely to be deposited with a plaque, so that the polymerizable composition of the present invention contributes to the prevention of root surface dental caries and the prevention of periodontal diseases. In addition, the cured product of the polymerizable composition of the present invention exhibits some excellent effects that the cured product has excellent abrasive resistance, maintains glaze for a long period of time, and further the cured product itself has little discoloration, so that the cured product also has excellent aesthetic appreciation.

BEST MODE FOR CARRYING OUT THE INVENTION

The fluorine compound (a) comprises a chain polymer having a main chain comprising a monomer unit having a hydrophilic group, and terminal groups comprising a fluoroalkyl group at each of both ends of the main chain.

In the fluorine compound (a), specific examples of the hydrophilic group owned by the chain polymer having a main chain comprising a monomer unit having a hydrophilic group, and terminal groups comprising a fluoroalkyl group at each of both ends of the main chain include, for example, a hydroxyl group, an amide group, an amino group, an alkylamino group, a polyoxyalkylene group, a morpholyl group, and a cyano group; acidic groups, such as a carboxylic acid group, a sulfonic acid group, a phosphonic acid group, and a phosphoric acid group, or salts thereof; quaternary ammonium salts group, such as a trimethylammonium chloride group, a pyridinium chloride group, and a pyridinium bromide group; amphoteric ion groups, such as an alkylbetaine group, a carboxybetaine group, a sulfobetaine group, and a phosphobetaine group; cyclic ether groups, such as an epoxy group, an oxetanyl group, and a tetrahydrofurfuryl group; an acetyl group, an acetocarbonyl group, and the like. Among them, acidic groups, such as a carboxylic acid group, a sulfonic acid group, a phosphonic acid group, and a phosphoric acid group, or salts thereof; quaternary ammonium salt groups, such as a trimethylammonium chloride group, a pyridinium chloride group, and a pyridinium bromide group; and amphoteric ion groups, such as an alkylbetaine group, a carboxybetaine group, a sulfobetaine group, and a phosphobetaine group, are preferable, from the viewpoint of having a high inhibitory effect of plaque adhesion.

Representative examples of the polymerizable monomer that is capable of constituting the monomer unit having a hydrophilic group include polymerizable monomers having a hydroxyl group, polymerizable monomers having an amide group, polymerizable monomers having an amino group or an aminoalkyl group, polymerizable monomers having a polyoxyalkylene group, polymerizable monomers having a morpholyl group, polymerizable monomers having an amphoteric ion, polymerizable monomers having a cyclic ether group, polymerizable monomers having a quaternary ammonium salt group, polymerizable monomers having a phosphoric acid group or a salt thereof, polymerizable monomers having a phosphonic acid group or a salt thereof, polymerizable monomers having a carboxylic acid group or a salt thereof, polymerizable monomers having a sulfonic acid group or a salt thereof, and the like. The present invention is not limited to those exemplified.

The polymerizable monomer having a hydroxyl group includes, for example, 2-hydroxyethyl (meth)acrylate, 3-hydroxypropyl (meth)acrylate, 10-hydroxydecyl (meth)acrylate, glycerol mono(meth)acrylate, N-methylol (meth)acrylamide, N-2-hydroxyethyl (meth)acrylamide, and the like. The term "(meth)acrylate" as used herein means both of "acrylate" and "methacrylate."

The polymerizable monomer having an amide group includes, for example, N-methylol (meth)acrylamide, N-vinyl-2-pyrrolidone, N-vinyl-2-piperidone, (meth)acrylamide, N,N-dimethyl (meth)acrylamide, and the like. The term "(meth)acrylamide" as used herein means both of "acrylamide" and "methacrylamide."

The polymerizable monomer having an amino group or an aminoalkyl group includes, for example, 2-aminoethyl (meth)acrylate, N,N-dimethylaminoethyl (meth)acrylate, and the like.

The polymerizable monomer having a polyoxyalkylene group includes, for example, a polyethylene glycol mono (meth)acrylate, and the like.

The polymerizable monomer having a morpholyl group includes, for example, (meth)acryloyl morpholine, and the like. The term "(meth)acryloyl morpholine" as used herein means both of "acryloyl morpholine" and "methacryloyl morpholine."

The polymerizable monomer having an amphoteric ion includes, for example, 2-(meth)acrylamide-2-methylpropanesulfonic acid, and the like.

The polymerizable monomer having a cyclic ether group includes, for example, tetrahydrofurfuryl (meth)acrylate, glycidyl (meth)acrylate, and the like.

The polymerizable monomer having a quaternary ammonium salt group includes, for example, 2-(meth)acryloyloxyethyl trimethylammonium chloride, 12-(meth)acryloyloxydodecyl pyridinium bromide, 2-(meth)acryloyloxyethyl dimethyloctylammonium chloride, and the like. The term "(meth)acryloyl" as used herein means both of "acryloyl" and "methacryloyl."

The polymerizable monomer having a phosphoric acid group or a salt thereof and the polymerizable monomer having a phosphonic acid group or a salt thereof include, for example, 2-(meth)acryloyloxyethyl dihydrogenphosphate, 4-(meth)acryloyloxybutyl dihydrogenphosphate, 6-(meth)acryloyloxyhexyl dihydrogenphosphate, 9-(meth)acryloyloxynonyl dihydrogenphosphate, 10-(meth)acryloyloxydecyl dihydrogenphosphate, 11-(meth)acryloyloxyundecyl dihydrogenphosphate, 12-(meth)acryloyloxydodecyl dihydrogenphosphate, 16-(meth)acryloyloxyhexadecyl dihydrogenphosphate, 2-(meth)acryloyloxyethylphenyl hydrogenphosphate, 2-(meth)acryloyloxyethylphenyl phosphonate, 10-(meth)acryloyloxydecyl phosphonic acid, and vinylphosphonic acid, alkali metal salts thereof, alkaline earth metal salts thereof, ammonium salts thereof, and the like.

The polymerizable monomer having a carboxylic acid group or a salt thereof includes, for example, maleic acid, itaconic acid, fumaric acid, (meth)acrylic acid, 4-(meth)acryloyloxyethoxycarbonyl phthalic acid, 4-(meth)acryloyloxybutyloxycarbonyl phthalic acid, 4-(meth)acryloyloxyhexyloxycarbonyl phthalic acid, 4-(meth)acryloyloxyoctyloxycarbonyl phthalic acid, 4-(meth)acryloyloxydecyloxycarbonyl phthalic acid, and acid anhydrides thereof; 10-(meth)acryloyloxy-1,1-decanedicarboxylic acid; 11-(meth)acryloyloxy-1,1-undecanedicarboxylic acid; alkali metal salts thereof, alkaline earth metal salts thereof, and ammonium salts thereof; and the like.

The polymerizable monomer having a sulfonic acid group or a salt thereof includes, for example, 2-(meth)acrylamide-2-methylpropanesulfonic acid, styrenesulfonic acid, 2-sulfoethyl (meth)acrylate, 10-sulfodecyl (meth)acrylate, 6-sulfohexyl (meth)acrylate, alkali metal salts thereof, alkaline earth metal salts thereof, and ammonium salts thereof, and the like.

Among the polymerizable monomers having a hydrophilic group, the monomers having a carboxylic acid group, such as (meth)acrylic acid and 4-(meth)acryloyloxyethoxycarbonyl phthalic acid; the polymerizable monomers having a phosphoric acid group such as 2-(meth)acryloyloxyethyl dihydrogenphosphate and 10-(meth)acryloyloxydecyl dihydrogenphosphate; the polymerizable monomers having a phosphonic acid group such as vinylphosphonic acid; the polymerizable monomers having a sulfonic acid group such as styrenesulfonic acid; the polymerizable monomers having an amphoteric ion such as 2-(meth)acrylamide-2-methylpropanesulfonic acid; and the polymerizable monomers having a quaternary ammonium salt group such as 2-(meth)acryloyloxyethyl trimethylammonium chloride, 12-(meth)acryloyloxydodecyl pyridinium bromide, 2-(meth)acryloyloxyethyl dimethyloctylammonium chloride are preferable.

The chain polymer having a monomer unit having a hydrophilic group includes a chain polymer obtained by polymerizing one or more polymerizable monomers having a hydrophilic group mentioned above.

The chain polymer having a monomer unit having a hydrophilic group includes, for example, chain polymers obtained by polymerizing at least one polymerizable monomers selected from 2-hydroxyethyl (meth)acrylate, 3-hydroxypropyl (meth)acrylate, 10-hydroxydecyl (meth)acrylate, glycerol mono(meth)acrylate, ethylene glycol mono(meth)acrylate, N-methylol (meth)acrylamide, N-2-hydroxyethyl (meth)acrylamide, N-methylol (meth)acrylamide, N-vinyl-2-pyrrolidone, N-vinyl-2-piperidone, (meth)acrylamide, N,N-dimethyl (meth)acrylamide, 2-(meth)acrylamide-2-methylpropanesulfonic acid, tetrahydrofurfuryl (meth)acrylate, glycidyl (meth)acrylate, (meth)acryloyl morpholine, N,N-dimethylaminoethyl (meth)acrylate, 2-aminoethyl (meth)acrylate, 2-(meth)acryloyloxyethyl dihydrogenphosphate, 4-(meth)acryloyloxybutyl dihydrogenphosphate, 6-(meth)acryloyloxyhexyl dihydrogenphosphate, 9-(meth)acryloyloxynonyl dihydrogenphosphate, 10-(meth)acryloyloxydecyl dihydrogenphosphate, 11-(meth)acryloyloxyundecyl dihydrogenphosphate, 12-(meth)acryloyloxydodecyl dihydrogenphosphate, 16-(meth)acryloyloxyhexadecyl dihydrogenphosphate, 2-(meth)acryloyloxyethylphenyl hydrogenphosphate, 2-(meth)acryloyloxyethylphenyl phosphonate, 10-(meth)acryloyloxydecyl phosphonic acid, vinylphosphonic acid, maleic acid, itaconic acid, fumaric acid, (meth)acrylic acid, 4-(meth)acryloyloxyethoxycarbonyl phthalic acid, 4-(meth)acryloyloxybutyloxycarbonyl phthalic acid, 4-(meth)acryloyloxyhexyloxycarbonyl phthalic acid, 4-(meth)acryloyloxyoctyloxycarbonyl phthalic acid, 4-(meth)acryloyloxydecyloxycarbonyl phthalic acid, and acid anhydrides thereof, 10-(meth)acryloyloxy-1,1-decanedicarboxylic acid, 11-(meth)acryloyloxy-1,1-undecanedicarboxylic acid, 2-(meth)acrylamide-2-methylpropanesulfonic acid, styrenesulfonic acid, 2-sulfoethyl (meth)acrylate, 10-sulfodecyl (meth)acrylate, 6-sulfohexyl (meth)acrylate, styrenesulfonic acid, 2-(meth)acryloyloxyethyl trimethylammonium chloride, 12-(meth)acryloyloxydodecyl pyridinium bromide, 2-(meth)acryloyloxyethyl dimethyloctylammonium chloride, and the like. Here, the term "(meth)acrylic acid" as used herein means both of "acrylic acid" and "methacrylic acid."

Among the chain polymers having a monomer unit having a hydrophilic group, chain polymers obtained by polymerizing at least one polymerizable monomers selected from the group consisting of (meth)acrylic acid, 4-(meth)acryloyloxyethoxycarbonyl phthalic acid, 2-(meth)acryloyloxyethyl dihydrogenphosphate, 10-(meth)acryloyloxydecyl dihydrogenphosphate, vinylphosphonic acid, styrenesulfonic acid, 2-(meth)acrylamide-2-methylpropanesulfonic acid, 2-(meth)acryloyloxyethyltrimethylammonium chloride, 12-(meth)acryloyloxydodecyl pyridinium bromide, and 2-(meth)acryloyloxyethyl dimethyloctylammonium chloride are preferable. In the case where the chain polymer is a copolymer, the chain polymer may be any one of random copolymers and block copolymers.

Here, the polymerizable monomer having a hydrophilic group may be copolymerized with a polymerizable monomer not having a hydrophilic group so long as the amount is within the range in which the object of the present invention is not hindered.

The polymerizable monomer not having a hydrophilic group includes, for example, methyl (meth)acrylate, ethyl (meth)acrylate, butyl (meth)acrylate, benzyl (meth)acrylate, lauryl (meth)acrylate, 3-(meth)acryloyloxypropyl trimethoxysilane, vinyl triethoxysilane, styrene, and the like. It is desired that the amount of the polymerizable monomer not having a hydrophilic group is usually within 50% by mol of the entire polymerizable monomers composed of the polymerizable monomer having a hydrophilic group and the polymerizable monomer not having a hydrophilic group subjected to the polymerization, preferably within 20% by mol, and even more preferably within 10% by mol, from the viewpoint of avoiding in significantly impairing the hydrophilicity of the overall fluorine compound (a).

Both ends of the chain polymer having a polymerization unit of the polymerizable monomer having a hydrophilic group can be protected with a terminal group containing a fluoroalkyl group by, for example, a method comprising the step of subjecting the both ends to block copolymerization according to a method such as anionic polymerization with the polymerizable monomer having a hydrophilic group, using a polymerizable monomer having a fluoroalkyl group as a side chain, thereby producing a block copolymer in which both ends are sealed with a polymer segment composed of the polymerizable monomer having a fluoroalkyl group; a method comprising the step of polymerizing with a polymerizable monomer having a hydrophilic group, using a peroxide having a fluoroalkyl group as a polymerization initiator as described in *Chemical Reviews*, 96(5) (1996), 1779-1808, or the like.

The fluoroalkyl group includes, for example, linear, branched, or cyclic fluoroalkyl groups having 1 to 12 carbon atoms.

Examples of the preferred fluoroalkyl group include a fluoroalkyl group represented by the formula: —$(CF_2)_m$F, wherein m is an integer of from 1 to 12, a perfluorocycloalkyl group, and the like. Among them, a —$CF_3$ group, a —$C_2F_5$ group, a —$C_3F_7$ group, a —$C_6F_{13}$ group, and a perfluorocyclohexyl group are preferable.

The number-average molecular weight of the fluorine compound (a) is preferably from 1,000 to 100,000, more preferably from 2,000 to 50,000, even more preferably from 4,000 to 20,000, even further preferably from 3,000 to 20,000, from the viewpoint of solubility to the polymerizable monomer (b) and the solvent (d) and anti-staining property.

Preferred examples of the fluorine compound (a) include a fluorine compound which is a chain polymer having a number-average molecular weight of from 1,000 to 100,000, the chain polymer having a main chain comprising a monomer unit having a hydrophilic group, and terminal groups containing a fluoroalkyl group on each of both ends of the main chain, wherein the main chain may contain monomer units other than the monomer unit having a hydrophilic group in a ratio of 50% by mol or less of the entire monomer units.

Preferred representative examples of the fluorine compound (a) include a fluorine compound having a number-average molecular weight of from 1,000 to 100,000, wherein the fluorine compound is represented by the formula (I):

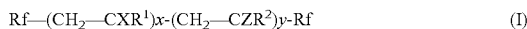

$$\text{Rf—}(CH_2\text{—}CXR^1)x\text{-}(CH_2\text{—}CZR^2)y\text{-Rf} \quad (I)$$

wherein each Rf is independently a fluoroalkyl group, or an organic group having a fluoroalkyl group at an end; each of $R^1$ and $R^2$ is independently a hydrocarbon group having 1 to 6 carbon atom, which may have a hydrogen atom or a halogen atom; X is a hydrophilic group, or a monovalent organic group having a hydrophilic group; and Z is a hydrogen atom, or a monovalent organic group other than X; each of x and y is independently a degree of polymerization as determined on the basis of its number-average molecular weight, wherein y/(x+y) is from 0 to 0.5; each of x number of —(CH$_2$—CXR$^1$)— groups and y number of —(CH$_2$—CZR$^2$)— group may be arranged in a random form or arranged in a block form. The fluorine compound represented by the formula (I) is preferable, from the viewpoint of providing easiness in its synthesis and excellent anti-staining property.

Representative examples of Rf include an organic group having a total number of carbon atoms of from 2 to 30, in which a fluoroalkyloxy group having 1 to 12 carbon atoms is positioned at its end; and a fluoroalkyloxy group having 1 to 12 carbon atoms. The fluoroalkyloxy group and the fluoroalkyl group may be linear, or may be branched.

Preferred examples of Rf include a fluoroalkyl group represented by the formula: —$(CF_2)_p$F, wherein p is an integer of from 1 to 12; and an organic group containing a fluoroalkyl group, the organic group represented by the formula: —CF(CF$_3$)O(CF$_2$CF(CF$_3$)O)$_q$C$_3$F$_7$, wherein q is an integer of from 0 to 6. Among them, a group represented by the formula: —CF(CF$_3$)OC$_3$F$_7$, a group represented by the formula: —CF(CF$_3$)OCF$_2$CF(CF$_3$)OC$_3$F$_7$, and a group represented by the formula: —CF(CF$_3$)OCF$_2$CF(CF$_3$)OCF$_2$CF(CF$_3$)OC$_3$F$_7$ are preferable, from the viewpoint of availability of a raw material peroxide, solubility to a solvent and a polymerizable monomer, and the like.

In addition, an Rf group represented by the formula: —COO—(CH$_2$)$_r$—(CF$_2$)$_p$—B, wherein p is an integer of from 1 to 8; r is an integer of from 0 to 2; B is a hydrogen atom or a fluorine atom is also preferable. Among them, a group represented by the formula: —COO—CH$_2$CF$_3$, a group represented by the formula: —COO—CH$_2$(CF$_2$)$_2$—H, a group represented by the formula: —COO—CH$_2$(CF$_2$)$_4$—H, a group represented by the formula: —COO—CH$_2$(CF$_2$)$_4$—F, a group represented by the formula: —COO—CH$_2$(CF$_2$)$_6$—H, a group represented by the formula: —COO—(CH$_2$)$_2$(CF$_2$)$_4$—H, and a group represented by the formula: —COO—(CH$_2$)$_2$(CF$_2$)$_4$—F are more preferable.

Each of R$^1$ and R$^2$ is independently a hydrocarbon group having 1 to 6 carbon atoms, which may have a hydrogen atom or a halogen atom. The hydrocarbon group having 1 to 6 carbon atoms which may have a halogen atom includes, for example, a methyl group, an ethyl group, a propyl group, a butyl group, a hexyl group, a cyclohexyl group, and a phenyl group and the like, each of which may have a halogen atom. It is preferable that R$^1$ and R$^2$ is a hydrogen atom, a methyl group, a phenyl group, or a trifluoromethyl group.

X is a hydrophilic group, or a monovalent organic group having a hydrophilic group. The hydrophilic group includes, for example, a hydroxyl group, an amide group, an amino group, an alkylamino group, a polyoxyalkylene group, a morpholyl group, a cyano group, acidic groups, such as a carboxylic acid group, a sulfonic acid group, a phosphonic acid group, and a phosphoric acid group, or salts thereof, quaternary ammonium salt groups, such as a trimethylammonium chloride group, a pyridinium chloride group, and a pyridinium bromide group, a sulfonium salt group, a pyrylium salt group, a phosphonium salt group, an iodonium salt group, amphoteric ion groups, such as an alkylbetaine group, a carboxybetaine group, a sulfobetaine group, and a phosphobetaine group; cyclic ether groups, such as an epoxy group, an oxetanyl group, and a tetrahydrofurfuryl group; an acetyl group, an acetocarbonyl group, and the like.

Among them, acidic groups, such as a carboxylic acid group, a sulfonic acid group, a phosphonic acid group, and a phosphoric acid group, or a salt thereof; quaternary ammonium salt groups, such as a trimethylammonium chloride group, a pyridinium chloride group, and a pyridinium bromide group; and amphoteric ion groups, such as an alkylbetaine group, a carboxybetaine group, a sulfobetaine group, and a phosphobetaine group, are preferable.

The monovalent organic group having a hydrophilic group means a portion corresponding to a side chain structure having a hydrophilic group of the side chain structure owned by the chain polymer obtained by polymerization of a polymerizable monomer having a hydrophilic group. For example, when 2-hydroxyethyl methacrylate is taken as an example of a polymerizable monomer having a hydrophilic group, the structure other than the methyl group of the structure other than the vinyl bond, i.e. a —COO—CH$_2$CH$_2$—OH group corresponds to X.

Specific examples of X include —(CH$_2$)$_a$—Y, wherein Y is a hydrophilic group (hereinafter the same); and a is an integer of from 1 to 16, —COO—(CH$_2$)$_b$—Y, wherein b is an integer of from 2 to 16, —COO—(CH$_2$CH$_2$O)$_c$—CH$_2$CH$_2$—Y, wherein c is an integer of from 1 to 20, —CONH—(CH$_2$)$_a$—Y, wherein a is as defined above, —COO—CHYCH$_2$—Y, —COO—CH$_2$—C(CH$_2$—Y)$_3$, —O—(CH$_2$)$_d$—Y, wherein d is an integer of from 2 to 12, —OCO—(CH$_2$)$_d$—Y, wherein d is as defined above),

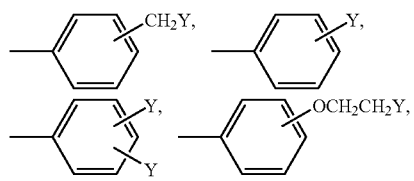

and the like. Among them, —COO—(CH$_2$)$_b$—Y, wherein b is as defined above, and —CONH—(CH$_2$)$_a$—Y, wherein a is an integer of from 1 to 6, are preferred.

Here, Y is a hydrophilic group, and examples thereof include a hydroxyl group, an amide group, an amino group, an alkylamino group, a polyoxyalkylene group, a morpholyl group, a cyano group, acidic groups, such as a carboxylic acid group, a sulfonic acid group, a phosphonic acid group, and a phosphoric acid group, or salts thereof, quaternary ammonium salt groups, such as a trimethylammonium chloride group, a pyridinium chloride group, and a pyridinium bromide group, a sulfonium salt group, a pyrylium salt group, a phosphonium salt group, an iodonium salt group, amphoteric ion groups, such as an alkylbetaine group, a carboxybetaine group, a sulfobetaine group, and a phosphobetaine group; cyclic ether groups, such as an epoxy group, an oxetanyl group, and a tetrahydrofurfuryl group; an acetyl group, an acetocarbonyl group, and the like. Among them, acidic groups, such as a carboxylic acid group, a sulfonic acid group, a phosphonic acid group, and a phosphoric acid group, or salts thereof; quaternary ammonium salt groups, such as a trimethylammonium chloride group, a pyridinium chloride group, and a pyridinium bromide group; and amphoteric ion groups, such as an alkylbetaine group, a carboxybetaine group, a sulfobetaine group, and a phosphobetaine group, are preferable.

The fluorine compound represented by the formula (I) can be easily synthesized, for example, by polymerizing a polymerizable monomer (f) having a hydrophilic group, the polymerizable monomer represented by the formula:

CH$_2$=CR$^1$X, wherein R$^1$ and X are as defined above, and optionally a polymerizable monomer not having a hydrophilic group, the polymerizable monomer represented by the formula:

CH$_2$=CR$^2$Z wherein R$^2$ and Z are as defined above, using a peroxide (e) represented by the formula:

Rf—COO—OCO—Rf wherein Rf is as defined above as a polymerization initiator.

It is preferable that the solubility of the polymerizable monomer having a hydrophilic group (f) in water at 15° C. is 10% by weight or more, and preferably 20% by weight or more, from the viewpoint of the anti-staining property and the inhibitory effect of plaque deposition, and improvements in the strength of a cured product, abrasion resistance, and the like.

Representative examples of the polymerizable monomer having a hydrophilic group (f) include a polymerizable monomer having a hydroxyl group, a polymerizable monomer having an amide group, a polymerizable monomer having an amino group or an aminoalkyl group, a polymerizable monomer having a polyoxyalkylene group, a polymerizable monomer having a morpholyl group, a polymerizable monomer having a cyclic ether group, a polymerizable monomer having an acidic group, such as a carboxylic acid group, a phosphoric acid group, a phosphonic acid group, or a sulfonic acid group, a polymerizable monomer having a quaternary ammonium salt group, a polymerizable monomer having an amphoteric ion, and the like.

The polymerizable monomer having a hydroxyl group includes, for example, 2-hydroxyethyl (meth)acrylate, 3-hydroxypropyl (meth)acrylate, 10-hydroxydecyl (meth)acrylate, glycerol mono(meth)acrylate, N-methylol (meth)acrylamide, N-2-hydroxyethyl (meth)acrylamide, and the like.

The polymerizable monomer having an amide group includes, for example, N-methylol (meth)acrylamide, N-vinyl-2-pyrrolidone, N-vinyl-2-piperidone, (meth)acrylamide, N,N-dimethyl (meth)acrylamide, and the like.

The polymerizable monomer having an amino group or an aminoalkyl group includes, for example, 2-aminoethyl (meth)acrylate, N,N-dimethylaminoethyl (meth)acrylate, and the like.

The polymerizable monomer having a polyoxyalkylene group includes, for example, polyethylene glycol mono (meth)acrylate, and the like.

The polymerizable monomer having a morpholyl group includes, for example, (meth)acryloyl morpholine, and the like.

The polymerizable monomer having a cyclic ether group includes, for example, tetrahydrofurfuryl (meth)acrylate, glycidyl (meth)acrylate, and the like.

Representative examples of the polymerizable monomer having a carboxylic acid group include a polymerizable monomer having a carboxylic acid group [—C(=O)OH] or an acid anhydride group [—C(=O)O—C(=O)—] in its molecule, and the like.

Specific examples of the polymerizable monomer having a carboxylic acid group include maleic acid, itaconic acid, fumaric acid, (meth)acrylic acid, 4-(meth)acryloyloxyethoxycarbonyl phthalic acid, 4-(meth)acryloyloxybutyloxycarbonyl phthalic acid, 4-(meth)acryloyloxyhexyloxycarbonyl phthalic acid, 4-(meth)acryloyloxyoctyloxycarbonyl phthalic acid, 4-(meth)acryloyloxydecyloxycarbonyl phthalic acid, 5-(meth)acryloylaminopentylcarboxylic acid, 6-(meth)acryloyloxy-1,1-hexanedicarboxylic acid, 8-(meth)acryloyloxy-1,1-octanedicarboxylic acid, 10-(meth)acryloyloxy-1,1-decanedicarboxylic acid, 11-(meth)acryloyloxy-1,1-undecanedicarboxylic acid, acid anhydrides thereof, alkali metal salts thereof, alkaline earth metal salts thereof, ammonium salts thereof, and the like.

Representative examples of the polymerizable monomer having a phosphoric acid group include polymerizable monomers having a phosphoric acid group, such as a phosphinico group [a =P(=O)OH group], or a phosphono group [a —P(=O)(OH)$_2$ group], a pyrophosphoric acid group [a —P(=O)(OH)—O—P(=O)(OH)— group], and the like.

Specific examples of the polymerizable monomer having a phosphoric acid group and the polymerizable monomer having a phosphonic acid group include 2-(meth)acryloyloxyethyl dihydrogenphosphate, 3-(meth)acryloyloxypropyl dihydrogenphosphate, 4-(meth)acryloyloxybutyl dihydrogenphosphate, 6-(meth)acryloyloxyhexyl dihydrogenphosphate, 8-(meth)acryloyloxyoctyl dihydrogenphosphate, 9-(meth)acryloyloxynonyl dihydrogenphosphate, 10-(meth)acryloyloxydecyl dihydrogenphosphate, 11-(meth)acryloyloxyundecyl dihydrogenphosphate, 12-(meth)acryloyloxydodecyl dihydrogenphosphate, 16-(meth)acryloyloxyhexadecyl dihydrogenphosphate, 20-(meth)acryloyloxyeicosyl dihydrogenphosphate, di[2-(meth)acryloyloxyethyl]hydrogenphosphate, di[10-(meth)acryloyloxydecyl]hydrogenphosphate, 1,3-di(meth)acryloyloxypropyl-2-dihydrogenphosphate, 2-(meth)acryloyloxyethylphenyl hydrogenphosphate, 2-(meth)acryloyloxyethyl 2-bromoethyl hydrogenphosphate, 2-(meth)acryloyloxyethylphenyl phosphonate, 10-(meth)acryloyloxydecylphosphonic acid, and the like;

"(5-methacryloxy)pentyl-3-phosphonopropionate, (6-methacryloxy)hexyl-3-phosphonopropionate, (10-methacryloxy)decyl-3-phosphonopropionate, (6-methacryloxy)hexyl-3-phosphonoacetate, and (10-methacryloxy)decyl-3-phosphonoacetate" listed in Japanese Patent Laid-Open No. Hei 3-294286, and the like; "2-methacryloyloxyethyl (4-methoxyphenyl)hydrogenphosphate, 2-methacryloyloxypropyl (4-methoxyphenyl)hydrogenphosphate, di[2-(meth)acryloyloxyethyl]pyrophosphate, di[4-(meth)acryloyloxybutyl]pyrophosphate, di[6-(meth)acryloyloxyhexyl]pyrophosphate, di[8-(meth)acryloyloxyoctyl]pyrophosphate, and di[10-(meth)acryloyloxydecyl]pyrophosphate" listed in Japanese Patent Laid-Open No. Sho 62-281885, and the like; and phosphoric acid group-containing polymerizable monomers, acid chlorides thereof, alkali metal salts thereof, and alkaline earth metal salts thereof and ammonium salts thereof, and the like, exemplified in Japanese Patent Laid-Open Nos. Sho 52-113089, Sho 53-67740, Sho 53-69494, Sho 53-144939, Sho 58-128393, and Sho 58-192891.

Representative examples of the polymerizable monomer having a sulfonic acid group include polymerizable monomers having a sulfo group (an —SO$_3$H group or an —OSO$_3$H group).

Specific examples of the polymerizable monomer having a sulfonic acid group include 2-(meth)acrylamide-2-methylpropanesulfonic acid, styrenesulfonic acid, 2-sulfoethyl (meth)acrylate, 10-sulfodecyl (meth)acrylate, 6-sulfohexyl (meth)acrylate, and the like, acid chlorides thereof, alkali metal salts thereof, alkaline earth metal salts thereof, and ammonium salts thereof, and the like.

Specific examples of the polymerizable monomer having a quaternary ammonium salt group include 2-(meth)acryloyloxyethyl trimethylammonium chloride, 12-(meth)acryloyloxydodecyl pyridinium bromide, 2-(meth)acryloyloxyethyl dimethyloctylammonium chloride, and the like.

Specific examples of the polymerizable monomer having an amphoteric ion group include 2-(meth)acrylamide-2-methylpropanesulfonic acid, and the like.

From the viewpoint that the fluorine compound (a) provides effects of even higher anti-staining property and inhibition of plaque deposition on the surface of the cured product, it is preferable that the polymerizable monomer (f) has as a hydrophilic group an acidic group, such as a carboxylic acid group, a sulfonic acid group, a phosphonic acid group, or a phosphoric acid group, or a salt thereof; a quaternary ammonium salt group, such as a trimethyl chloride group, a pyridinium chloride group, or a pyridinium bromide group; or an amphoteric ion group, such as an alkylbetaine group, a carboxybetaine group, a sulfobetaine group, or a phosphobetaine group. The above-mentioned fluorine compound having a hydrophilic group (a) can be easily obtained by using the above-mentioned polymerizable monomer having a hydrophilic group.

Any one of the polymerizable monomers having a hydrophilic group (f) may be used alone or in a mixture of two or more kinds, respectively. Especially, when two or more kinds of polymerizable monomers having an acidic group are used in a mixture as the polymerizable monomers having a hydrophilic group, it is desired that at least one kind is a polymerizable monomer having a carboxylic acid group. Further, in this case, as the polymerizable monomer having a carboxylic acid group, (meth)acrylic acid is especially preferable. In the combination as mentioned above, the value of a molar ratio of (meth)acrylic acid and another polymerizable monomer having an acidic group, i.e. (meth)acrylic acid/another polymerizable monomer, is within the range of from 0.5 to 100, preferably from 1 to 50, and even more preferably from 2 to 10.

Incidentally, as the polymerizable monomer (f), a polymerizable monomer not having a hydrophilic group, for example, a hydrophobic monomer such as methyl (meth)acrylate, butyl (meth)acrylate, (meth)acryloyloxypropyl trimethoxysilane, or vinyltrimethoxysilane, may be used within the range that would not impair the anti-staining property. In a case where a hydrophobic monomer is used, usually, the amount of the hydrophobic monomer is preferably 50% by mol or less, and more preferably 20% by mol or less, based on the entire amount of the polymerizable monomer subjected to the polymerization.

The peroxide (e) is used as a polymerization initiator. Preferred examples of the peroxide (e) includes a peroxide represented by the formula: Rf—COO—OCO—Rf, wherein Rf is as defined above.

As a method for producing a fluorine compound represented by the formula (I) comprising polymerizing a polymerizable monomer (f) using a fluoroalkanoyl peroxide as a peroxide (e), a usual polymerization method in which a peroxide is used as a polymerization initiator can be applied. More specifically, a fluorine compound represented by the formula (I) can be produced by, for example, polymerizing a polymerizable monomer (f) and optionally a hydrophobic monomer in an inactive solvent such as a halogenated aliphatic hydrocarbon in the presence of a fluoroalkanoyl peroxide under normal pressure at a temperature of 0° to 150° C.

Also, an alternative method for producing a fluorine compound (a) includes, for example, a method of subjecting the above-mentioned polymerizable monomer (f), or a mixed monomer of the polymerizable monomer (f) and a hydrophobic monomer to a block polymerization with a fluorine-containing monomer having a perfluoroalkyl group as its side chain, and the like.

Preferred examples of the above-mentioned fluorine-containing monomers include fluoro (meth)acrylates, such as 1H,1H,2H,2H-nonylfluorohexyl (meth)acrylate, 1H,1H,2H,2H-tridecafluorooctyl (meth)acrylate, 1H,1H,2H,3H,3H-2-hydroxy-tridecafluorononyl (meth)acrylate, 1H,1H,2H,2H-undecafluoro-5-methylhexyl (meth)acrylate, 1H,1H,5H-octafluoropentyl (meth)acrylate, 1H,1H,6H-decafluorohexyl (meth)acrylate, 1H,1H,7H-dodecafluoroheptyl (meth)acrylate, 1H,1H,9H-hexadecafluorononyl (meth)acrylate, 1H,1H,3H-hexafluorobutyl (meth)acrylate, 1H,1H,2H,2H,7H-decafluoroheptyl (meth)acrylate, and 1H,1H,2H,4H,7H-decafluoroheptyl methacrylate, and the like. Each of these fluorine-containing monomers can be used alone or in a mixture of two or more kinds.

It is desired that the amount of the fluorine compound (a) is preferably from 0.001 to 30 parts by weight, and preferably from 0.01 to 10 parts by weight, based on 100 parts by weight of the polymerizable monomer (b), from the viewpoint of anti-staining property, an effect of inhibiting the deposition of plaque, and strength and abrasion resistance of a cured product.

The kinds of the polymerizable monomer (b) and the polymerization initiator (c) that are usable in the present invention are not particularly limited, and those that are generally employed can be used. In general, the kinds of these monomers and the polymerization initiator include a combination of a radical polymerizable monomer and a radical polymerization initiator (radical polymerizable composition); a combination of a cationic polymerizable monomer and a cationic polymerization initiator (cationic polymerizable composition); and the like.

Specific examples of the radical polymerizable monomer in the polymerizable monomer (b) include esters derived from unsaturated carboxylic acids, such as α-cyanoacrylic acid, (meth)acrylic acid, α-halogenated acrylic acid, crotonic acid, cinnamic acid, sorbic acid, maleic acid, and itaconic acid; (meth)acrylamide, (meth)acrylamide derivatives, vinyl esters, vinyl ethers, mono-N-vinyl derivatives, and styrene derivatives; and the like. Among them, (meth)acrylic esters are preferred.

Examples of (meth)acrylic ester-based polymerizable monomers are given hereinbelow.

(1) The monofunctional (meth)acrylates includes:

Methyl (meth)acrylate, isobutyl (meth)acrylate, benzyl (meth)acrylate, lauryl (meth)acrylate, 2-(N,N-dimethylamino)ethyl (meth)acrylate, 2,3-dibromopropyl (meth)acrylate, 3-methacryloyloxypropyl trimethoxysilane, 2-hydroxyethyl (meth)acrylate, 6-hydroxyhexyl (meth)acrylate, 10-hydroxydecyl (meth)acrylate, propylene glycol mono (meth)acrylate, glycerol mono(meth)acrylate, erythritol mono(meth)acrylate, N-methylol (meth)acrylamide, N-hydroxyethyl (meth)acrylamide, N,N-bis(hydroxyethyl) (meth) acrylamide, (meth)acryloyloxydodecylpyridinium bromide, (meth)acryloyloxydodecylpyridinium chloride, (meth)acryloyloxydodecylpyridinium bromide, (meth)acryloyloxyhexadecylpyridinium chloride, and the like.

(2) The bifunctional (meth)acrylates include:

Ethylene glycol di(meth)acrylate, triethylene glycol di(meth)acrylate, propylene glycol di(meth)acrylate, neopentyl glycol di(meth)acrylate, 1,6-hexanediol di(meth)acrylate, 1,10-decanediol di(meth)acrylate, bisphenol A diglycidyl (meth)acrylates (so-called BisGMA), 2,2-bis[4-(meth) acryloyloxyethoxyphenyl]propane, 2,2-bis[4-(meth) acryloyloxypolyethoxyphenyl]propane, 2,2-bis[4-[3-(meth) acryloyloxy-2-hydroxypropoxy]phenyl]propane, 1,2-bis[3-(meth)acryloyloxy-2-hydroxypropoxy]ethane, pentaerythritol di(meth)acrylate, 1,2-bis(3-methacryloyloxy-2-hydroxypropoxy)ethane, [N,N'-(2,2,4-trimethylhexamethylene)bis(2-carbamoyloxyethyl)]dimethacrylate, and the like.

(3) The trifunctional or higher polyfunctional (meth)acrylates include:

Trimethylolpropane tri(meth)acrylate, trimethylolethane tri(meth)acrylate, tetramethylolmethane tri(meth)acrylate, pentaerythritol tetra(meth)acrylate, dipentaerythritol hexa (meth)acrylate, [N,N'-(2,2,4-trimethylhexamethylene)bis[2-(aminocarbonyloxy)propane-1,3-diol]]tetramethacrylate, 1,7-diacryloyloxy-2,2,6,6-tetraacryloyloxymethyl-4-oxaheptane, and the like.

Any one of the above-mentioned polymerizable monomers can be used alone or in a mixture of two or more kinds.

Here, when the adhesion of dentine, a metal, a ceramic or the like to a substrate is to be improved, in some cases it is a preferred embodiment that a functional monomer that gives the adhesion to these substrates may be contained in the polymerizable composition of the present invention as a part of the polymerizable monomer (b).

As functional monomers, for example, monomers having a phosphoric acid group, such as 2-(meth)acryloyloxyethyl dihydrogenphosphate, 10-(meth)acryloyloxydecyl dihydrogenphosphate, and 2-(meth)acryloyloxyethyl phenyl hydrogenphosphate, and monomers having a carboxylic acid group, such as 11-(meth)acryloyloxy-1,1-undecanedicarboxylic acid and 4-(meth)acryloyloxyethoxycarbonyl phthalic acid are preferred because the monomers show excellent adhesion to dentine and a base metal.

As the functional monomers, for example, 10-mercaptodecyl (meth)acrylate, 6-[3-(4-vinylbenzyl)propylamino]-1,3,5-triazine-2,4-dithione, thiouracil derivatives described in Japanese Patent Laid-Open No. Hei 10-1473, and compounds containing the element sulfur described in Japanese Patent Laid-Open No. Hei 11-92461 are preferred because the compounds show excellent adhesion to a precious metal.

Further, as a functional monomer, for example, a silane coupling agent such as 3-methacryloyloxypropyl trimethoxysilane is effective in adhesion to a ceramic, porcelain, or a dental composite resin.

It is preferable that the amount of the functional monomer is from 0.1 to 80 parts by weight, based on 100 parts by weight of the entire polymerizable monomer (b), from the viewpoint of adhesive strength and adhesive durability to the substrate.

In the polymerizable composition of the present invention, it is preferable that a polymerization initiator (c) is previously added so as to facilitate the polymerization curing.

As the polymerization initiator (c) which is used in combination with the above-mentioned radical polymerizable monomer, a known radical polymerization initiator, such as a hot polymerization initiator, an ambient-temperature polymerization initiator, a photopolymerization initiator, can be used.

The hot polymerization initiator includes polymerization initiators such as peroxides and azo compounds, of which operable temperature range is from 40° to 100° C. Specific examples of the hot polymerization initiator include organic peroxides, such as diacyl peroxides, peroxyesters, dialkyl peroxides, peroxyketals, ketone peroxides, and hydroperoxides.

The diacyl peroxides include, for example, benzoyl peroxide, 2,4-dichlorobenzoyl peroxide, m-toluoyl peroxide, and the like.

The peroxyesters include, for example, t-butyl peroxybenzoate, bis-t-butyl peroxyisophthalate, 2,5-dimethyl-2,5-bis(benzoylperoxy)hexane, t-butylperoxy-2-ethyl hexanoate, t-butyl peroxyisopropylcarbonate, and the like.

The dialkyl peroxides include, for example, dicumyl peroxide, di-t-butyl peroxide, lauroyl peroxide, and the like.

The peroxyketals include, for example, 1,1-bis(t-butylperoxy) 3,3,5-trimethylcyclohexane, and the like.

The ketone peroxides include, for example, methyl ethyl ketone peroxide, and the like.

The hydroperoxides include, for example, t-butyl hydroperoxide, and the like.

As the ambient-temperature polymerization initiator, for example, a redox polymerization initiator system composed of an oxidizing agent (polymerization initiator) and a reducing agent (accelerating agent) can be favorably used. In this case, for example, benzoyl peroxide can be used as a polymerization initiator, and an aromatic tertiary amine, such as diethanol toluidine, or an aromatic sulfinate can be used as an accelerating agent.

When a redox polymerization initiator is used, it is preferable that the polymerizable composition of the present invention takes the form in which two or more divided portions are wrapped. As the oxidizing agent in the redox polymerization initiator system, for example, the organic peroxides, such as diacyl peroxides, peroxy esters, dialkyl peroxides, peroxyketals, ketone peroxides, and hydroperoxides, mentioned above are preferred.

As the reducing agent, for example, an aromatic tertiary amine, an aliphatic tertiary amine, and sulfinic acid or a salt thereof, or the like, are preferred.

The aromatic tertiary amines include, for example, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, 2-butoxyethyl 4-dimethylaminobenzoate, 2-methacryloyloxyethyl 4-dimethylaminobenzoate, and the like. Each of these aromatic tertiary amines can be used alone or in a mixture of two or more kinds.

The aliphatic tertiary amines include, for example, trimethylamine, triethylamine, N-methyldiethanolamine, N-ethyldiethanolamine, N-n-butyldiethanolamine, N-lauryldiethanolamine, triethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, and the like. Each of these aliphatic tertiary amines can be used alone or in a mixture of two or more kinds.

The sulfinic acids or salts thereof include, for example, benzenesulfinic acid, sodium benzenesulfinate, potassium benzenesulfinate, calcium benzenesulfinate, lithium benzenesulfinate, toluenesulfinic acid, sodium toluenesulfinate, potassium toluenesulfinate, calcium toluenesulfinate, lithium toluenesulfinate, 2,4,6-trimethylbenzenesulfinic acid, sodium 2,4,6-trimethylbenzenesulfinate, potassium 2,4,6-trimethylbenzenesulfinate, calcium 2,4,6-trimethylbenzenesulfinate, lithium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, calcium 2,4,6-triethylbenzenesulfinate, 2,4,6-isopropylbenzenesulfinic acid, sodium 2,4,6-triisopropylbenzenesulfinate, potassium 2,4,6-triisopropylbenzenesulfinate, calcium 2,4,6-triisopropylbenzenesulfinate, and the like. Each of these sulfinic acids or salts thereof can be used alone or in a mixture of two or more kinds.

As the photopolymerization initiator, a photopolymerization initiator which is excited with light having a wavelength of from 350 to 700 nm is preferable because a photoirradiation device in a visible light range, which has been conventionally widely used, can be used without necessitating a specialized photoirradiation device (for example, an ultraviolet ray irradiation device).

The photopolymerization initiator which is excited with light having a wavelength of from 350 to 700 nm includes, for example, α-diketones, ketals, thioxanthones, acyl phosphine oxides, coumarins, halomethyl group-substituted s-triazine derivatives, and the like.

Examples of the above-mentioned α-diketones include camphor quinone, benzyl, 2,3-pentanedione, and the like.

Examples of the above-mentioned ketals include benzyl dimethyl ketal, benzyl diethyl ketal, and the like.

Examples of the above-mentioned thioxanthones include 2-chlorothioxanthone, 2,4-diethylthioxanthone, and the like.

Examples of the above-mentioned acyl phosphine oxides include 2,4,6-trimethylbenzoyl diphenylphosphine oxide, 2,6-dimethoxybenzoyl diphenylphosphine oxide, 2,6-dichlorobenzoyl diphenylphosphine oxide, 2,3,5,6-tetramethylbenzoyl diphenylphosphine oxide, benzoylbis(2,6-dimethylphenyl) phosphonate, 2,4,6-trimethylbenzoyl ethoxyphenylphosphine oxide, and water-soluble acyl phosphine oxide compounds disclosed in Japanese Examined Publication Hei 3-57916, and the like.

Examples of the above-mentioned coumarins include compounds disclosed in Japanese Patent Laid-Open No. Hei 10-245525, such as 3,3'-carbonylbis(7-diethylamino)coumarin, 3-(4-methoxybenzoyl)coumarin, and 3-thienoyl coumarin.

Examples of the above-mentioned halomethyl group-substituted s-triazine derivatives include compounds disclosed in Japanese Patent Laid-Open No. Hei 10-245525, such as 2,4,6-tris(trichloromethyl)-s-triazine, 2,4,6-tris(tribromomethyl)-s-triazine, and 2-methyl-4,6-bis(trichloromethyl)-s-trizaine, and the like.

Any one of the photopolymerization initiators may be used alone or in a mixture of two or more kinds.

It is desired that the amount of the above-mentioned radical polymerization initiator is usually from 0.01 to 10 parts by weight, preferably from 0.05 to 5 parts by weight, and even more preferably from 0.1 to 3 parts by weight, based on 100 parts by weight of the polymerizable monomer (b).

Incidentally, when a photopolymerization initiator is used, it is preferable that the photopolymerization initiator and a reducing agent are used together in order to accelerate the photo-curing property.

The reducing agent primarily includes tertiary amines, aldehydes, compounds having a thiol group, and the like. Each of these reducing agents can be used alone or in a mixture of two or more kinds.

Examples of the tertiary amines include 2-dimethylaminoethyl (meth)acrylate, N,N-bis[(meth)acryloyloxyethyl]-N-methylamine, ethyl 4-dimethylaminobenzoate, butyl 4-dimethylaminobenzoate, butoxyethyl 4-dimethylaminobenzoate, N-methyldiethanolamine, 4-dimethylaminobenzophenone, and the like.

Examples of the aldehydes include dimethylaminobenzaldehyde, terephthalaldehyde, and the like.

Examples of the compounds having a thiol group include 2-mercaptobenzoxazole, decanethiol, 3-mercaptopropyltrimethoxysilane, thiobenzoic acid, and the like.

It is desired that the amount of the reducing agent is usually from 0.01 to 10 parts by weight, preferably from 0.05 to 5 parts by weight, and more preferably from 0.1 to 3 parts by weight, based on 100 parts by weight of the polymerizable monomer (b).

As the polymerizable composition of the present invention, besides the radical polymerizable composition containing a radical polymerizable monomer and a radical polymerization initiator as mentioned above, a cationic polymerizable composition containing a cationic polymerizable monomer as the polymerizable monomer (b), and a cationic polymerization initiator as the polymerization initiator (c) can be also used. The cationic polymerizable monomer includes, for example, cationic polymerizable vinyl compounds, lactones, cyclic ethers, and the like.

The cationic polymerizable vinyl compound includes, for example, vinyl ethers and styrene derivatives, such as ethylene glycol divinyl ether, glycerol trivinyl ether, trimethylolpropane trivinyl ether, 4-vinyl ether styrene, and allyl vinyl ether.

The lactones include cyclic lactones such as γ-propiolactone and ε-caprolactone.

The cyclic ethers include, for example, alicyclic epoxy compounds, oxetane compounds, spiro orthoesters, bicyclo-orthoesters, cyclic carbonates, and the like. Among them, the alicyclic epoxy compounds and the oxetane compounds are preferable.

Examples of the alicyclic epoxy compounds include 3,4-epoxycyclohexyl methyl-3',4'-epoxycyclohexane carboxylate [products manufactured by Union Carbide Corporation under the trade name of UVR6105 (low-viscosity product) and UVR6110 (low-viscosity product), a product manufactured by DAICEL CHEMICAL INDUSTRIES, LTD. under the trade name of CELLOXIDE 2021, and the like], bis(3,4-epoxycyclohexylmethyl) adipate [a product manufactured by Union Carbide Corporation under the trade name of UVR 6128], vinylcyclohexene monoepoxide [a product manufactured by DAICEL CHEMICAL INDUSTRIES, LTD. under the trade name of CELOXIDE 2000], ε-caprolactone-modified 3,4-epoxycyclohexylmethyl 3',4'-epoxycyclohexanecarboxylate [a product manufactured by DAICEL CHEMICAL INDUSTRIES, LTD. under the trade name of CELOXIDE 2081], 1-methyl-4-(2-methyloxiranyl)-7-oxabicyclo[4.1.0]heptane [a product manufactured by DAICEL CHEMICAL INDUSTRIES, LTD. under the trade name of CELOXIDE 3000], and the like.

Examples of the oxetane compound include oxetanes such as 3-ethyl-3-hydroxymethyloxetane, 1,4-bis{[(3-ethyl-3-oxetanyl)methoxy]methyl}benzene, 3-ethyl-3-(phenoxymethyl)oxetane, 3-ethyl-3-(2-ethylhexyloxymethyl)oxetane, and di[1-ethyl(3-oxetanyl)]methyl ether. These compounds can be easily made available, for example, from TOAGOSEI CO., LTD. Incidentally, when the oxetane compound is used together with the above-mentioned alicyclic epoxy compound, the curing property can be further improved in some cases.

As the cationic polymerization initiator a photo-cationic polymerization initiator is preferable. Examples of the photo-cationic polymerization initiator include known sulfonium salts, ammonium salts, and the like, and diaryl iodonium salts, triaryl sulfonium salts, and the like, which can be properly selected from those described in Japanese Patent Laid-Open Nos. Hei 6-298912, Hei 8-143806, Hei 8-283320, and the like and used.

In addition, as the photo-cationic polymerization initiator, commercially available products can be directly used. Representative examples of the commercially available product include products manufactured by Nippon Soda Co., Ltd under the trade names of CI-1370, CI-2064, CI-2397, CI-2624, CI-2639, CI-2734, CI-2758, CI-2823, CI-2855, CI-5102, and the like; products manufactured by Rhodia under the trade names of PHOTOINITIATOR 2047, and the like; products manufactured by Union Carbide Corporation under the trade names of UVI-6974, UVI-6990, and the like, and the present invention is not limited to those exemplified.

The amount of the cationic polymerization initiator used may differ depending upon its kind, the kind of the cationic polymerizable compound used, and compositional ratio therebetween, operating conditions, and the like. It is desired that the amount of the cationic polymerization initiator used is usually from 0.1 to 20 parts by weight, preferably from 1 to 10 parts by weight, and more preferably from 1 to 5 parts by weight, based on 100 parts by weight of the cationic polymerizable compound, from the viewpoint of improving the curing property and enhancing the storage stability.

In addition, a composition comprising an epoxy compound and a hydroxyl group-containing compound, as described in Japanese Unexamined Patent Publication Nos. Hei 10-508067, 2001-520758, 2001-520759, and the like, can be applied as a polymerizable monomer in the present invention to a system in which the polymerizable monomer is cured in the presence of a photopolymerization catalyst comprising a iodonium salt (polymerization initiator) and a visible light ray sensitizing agent (accelerator).

In the present invention, a more preferred embodiment of the polymerizable composition is a composition in which a solvent (d) is further added to a fluorine compound (a), a polymerizable monomer (b), and a polymerization initiator (c).

The solvent (d) as referred to herein is a liquid which has a boiling point at a normal pressure within the range of from 40° to 180° C., and includes, for example, water, alcohols such as methanol, ethanol, isopropanol, n-propanol, butanol, and cyclohexanol; halogenated compounds such as chloroform, methylene chloride, and chlorobenzene; hydrocarbons such as hexane, cyclohexane, toluene, and xylene; ketones such as acetone, methyl ethyl ketone, cyclohexanone; esters such as ethyl acetate and butyl acetate; ethers; and the like, and the present invention is not limited only to those exemplified.

In the polymerizable composition of the present invention, the advantages in the use of a solvent as described above are that a fluorine compound can be easily dissolved in the composition, and further that after a polymerizable composition is applied to a substrate, the fluorine compound can be localized on the surface (vapor-liquid interface) of the polymerizable composition during the course of the evaporation of the solvent, whereby the layer composed of the fluorine compound is densely formed on the surface after curing, so that the surface shows an even higher anti-staining property, or the like. From these viewpoints, a solvent having excellent compatibility with the fluorine compound and being capable of relatively easily evaporating after coating, for example, water, methanol, ethanol, propanol, butanol, acetone, or the like is preferred.

It is preferred that the amount of the solvent (d) is usually from 30 to 1000 parts by weight, preferably from 50 to 500 parts by weight, and more preferably from 100 to 300 parts by weight, based on 100 parts by weight of the polymerizable monomer (b).

In addition, when the composition ratio of each of the components (a) to (d) in the polymerizable composition of the present invention is comprehensively shown, it is desired that the amount of the fluorine compound (a) is from 0.001 to 30 parts by weight, and preferably from 0.01 to 10 parts by weight, that the amount of the polymerization initiator (c) is from 0.05 to 10 parts by weight, and preferably from 0.1 to 5 parts by weight, and that the amount of the solvent (d) is from 30 to 1000 parts by weight, and preferably from 50 to 500 parts by weight, based on 100 parts by weight of the polymerizable monomer (b).

In the polymerizable composition of the present invention, when constituents that would cause interactions to each other in a dissolved state are used, a method in which the constituents that would cause interactions to each other are previously divided and wrapped individually, and both components are mixed to polymerize before use, in order to increase the storage stability near an ambient temperature may be employed. Especially, when a redox polymerization catalyst comprising a peroxide and a reducing agent is used as a polymerization initiator system, the peroxide and the reducing agent are separately wrapped, and the both components are weighed, and mixed before use, whereby the polymerization and curing can be carried out.

On the other hand, when a photopolymerization initiator is used as a polymerization initiator, a polymerizable composition can be supplied to a user in a single-liquid state in which all the constituents are dissolved because the polymerizable composition of the present invention containing the photopolymerization initiator would be stored in a sufficiently light-shaded container, whereby the storage stability can be enhanced. Moreover, since the user can apply the composition inside the container directly to teeth or a restorative material, there is an advantage that its operation is convenient. Use embodiment benefiting this advantage includes, for example, a single-liquid type dental coating agent in which a dental polymerizable composition is wrapped together in a single wrapping.

As mentioned above, when a solvent is used in the polymerizable composition of the present invention, it is preferable that a polymerizable monomer that does not dissolve a fluorine compound (a) is selected as a polymerizable monomer (b), from the viewpoint of even more localizing the fluorine compound (a) to the surface of the cured product, and that in a state where a solvent is blended, each of the polymerizable monomer (b) and the solvent (d) is adjusted in its kind and amount, so that the fluorine compound (a) is evenly dissolved. By selecting the combination as described above, as the solvent is evaporated and dissipated after applying the coating agent, an action of the fluorine compound (a) to be precipitated on the surface of the polymerizable composition is added, whereby an even more dense layer composed of the fluorine compound (a) can be formed on the surface of the cured product.

The method for forming an even more dense layer composed of a fluorine compound on the surface of the cured product as described above includes, for example, a method including the steps of applying a polymerizable composition of the present invention to the surface of teeth or a dental restorative material, evaporating a solvent contained in the polymerizable composition, and curing the polymerizable composition, and a method of curing a polymerizable composition by photoirradiation is preferred, from the viewpoint of convenience of the operation.

To the polymerizable composition of the present invention, a filler, an ultraviolet ray absorbent, an antioxidant, a polymerization inhibitor, a colorant, an antibacterial agent, an X-ray contrast agent, a thickening agent, a fluorescent agent, or the like can be further added, depending upon its purpose.

For example, when fluorine ion sustain-releasability is expected from the cured surface, a fluorine ion sustain-releasable filler, such as fluoroaluminosilicate glass filler, calcium fluoride, sodium fluoride, or sodium monofluorophosphate can be added.

When antibacterial property is expected, for example, a surfactant having an antibacterial activity, such as cetylpyridinium chloride or 12-(meth)acryloyloxydodecylpyridinium bromide, or a photocatalytic titanium oxide can be added.

When imparted with X-ray opacity property, a glass filler containing a heavy metal element such as barium, ytterbium, strontium, or lanthanum (for example, barium boroaluminosilicate glass, or the like), a fine powder composed of ytterbium fluoride, barium sulfate, or the like can be added.

When the viscosity and the coatability are adjusted, a thickening agent such as sodium polyacrylate, sodium alginate, or gum arabic, or a microfiller silica having an average particle size of 0.1 µm or less [for example, a product manufactured by Nippon Aerosil Co, Ltd. under the trade name of Aerosil] can be added.

When a dental composite resin is prepared using the polymerizable composition of the present invention, a filler is further blended.

The fillers are roughly classified into organic fillers and inorganic fillers.

Examples of the organic filler include polymers such as methyl polymethacrylate, ethyl polymethacrylate, methyl methacrylate-ethyl methacrylate copolymers, a crosslinked methyl polymethacrylate, a crosslinked ethyl polymethacrylate, ethylene-vinyl acetate copolymers, and styrene-butadiene copolymers; fluororesins such as polytetrafluoroethylene (PTFE), tetrafluoroethylene-ethylene copolymers, tetrafluoroethylene-hexafluoropropylene copolymers (FEP), poly(vinylidene) fluoride (PVDF), and polychlorotrifluoroethylene (PCTFE), and each of these organic fillers can be used alone or in a mixture of two or more kinds.

Examples of the inorganic filler include various kinds of glasses [containing silicon dioxide (quartz, quartz glass, silica gel, or the like), alumina, or silicon as a main component, and containing boron and/or aluminum together with various kinds of heavy metals], various kinds of ceramics, diatomaceous earth, kaolin, clay minerals (montmorillonite, or the like), activated white clay, synthetic zeolite, mica, calcium fluoride, ytterbium fluoride, calcium phosphate, barium sulfate, zirconium dioxide, titanium dioxide, hydroxyapatite, and the like, and each of these inorganic fillers can be used alone or in a mixture of two or more kinds.

In addition, there would not be any disadvantages if an organic-inorganic composite filler obtainable by previously adding a polymerizable monomer to these inorganic fillers, forming the mixture in a paste-like state, polymerizing the polymerizable monomer, curing the product, and pulverizing the cured product may be used.

The amount of the filler is properly determined in consideration of the operability (viscosity) of the paste, and the mechanical strength. It is desired that the amount of filler is usually from 10 to 1800 parts by weight, and preferably from 50 to 1500 parts by weight, based on 100 parts by weight of a total of the above-mentioned fluorine compound (a), the above-mentioned polymerizable monomer (b), and the polymerization initiator (c).

Specific examples of the applications of the dental polymerizable composition of the present invention include dental composite resins, such as dental composite filler materials, crowning materials, and bonding materials; dental adhesive agents, such as teeth-straightening adhesive agents, cavity-coating adhesive agents, and tooth fissure sealing materials; denture base materials, denture base mucosal adjusting materials, fissure sealants, coating agents applied to tooth surface or dental prosthetic, surface glazes, and the like. When a solvent is contained as mentioned above, since a hard, thin coating film can be formed after curing, the dental polymerizable composition can be suitably used for various coating applications, for example, a fissure sealant, a dental coating agent to tooth surface or dental prosthetic, surface stains or a surface glaze, a hypersensitive inhibitor, a dental manicure, or the like.

When the dental polymerizable composition of the present invention is used as a coating agent to tooth surface or a dental restorative material, various pretreatments can be provided in order to enhance adhesion to the surface. For example, when the dental polymerization composition is applied to natural teeth in the oral cavity, an etching treatment with an aqueous phosphoric acid may be provided, or an adhesive primer or a bonding agent in which a functional monomer having adhesive property to tooth structure is blended can also be previously applied to the natural teeth.

In addition, when the substrate is made of ceramics, a composite resin, a metal or the like, a sand-blast treatment or a primer treatment containing a silane coupling agent or a phosphate monomer can be provided. In addition, in the case of a resin such as a denture base resin, where the substrate is made of polymethyl methacrylate (PMMA), a polycarbonate, or the like, a treatment of applying a solvent having a strong permeability of methylene chloride or the like to swell the substrate can be provided.

EXAMPLES

The present invention will be specifically described hereinbelow by the Examples, without intending to limit the scope of the present invention thereto.

[Anti-Staining Property Test]

A color test was conducted with a turmeric pigment using a bovine tooth enamel as a substrate. As a means of conveniently evaluating the coloration of the dental materials in the oral cavity simulatively, the anti-staining property using turmeric was evaluated in reference to the evaluation method described in *Nippon Hotetsu Shika Gakkaishi* (*PROSTHODONTIC RESEARCH & PRACTICE*), 35 (1991), 542-555 by Takamata, et al.

Bovine front teeth were subjected to wet grinding to be smooth with #1000 silicon carbide paper, to prepare an enamel smooth surface. A 35% aqueous phosphoric acid solution was applied to the surface, and allowed to stand for 30 seconds. The surface was washed with running water, and subjected to an etching treatment. A polymerizable composition was applied in a single layer on a side of the surface dried with an air syringe, and volatile components are slowly evaporated and dissipated. Thereafter, the surface was subjected to photoirradiation with a dental photoirradiator [manufactured by J. MORITA TOKYO MFG. CORP. under the trade name of JETLITE 3000] until an unpolymerized layer on the surface disappeared, to polymerize and cure the coated composition.

In order to evaluate the anti-staining property of this coated layer, a coloring test using an edible pigment turmeric was conducted. Specifically, a test piece prepared was allowed to stand in an aqueous suspension containing 1% by weight of turmeric pigment with the coated side facing up, and kept in the dark at 37° C. After 24 hours, the test piece was taken out, washed with water, and the chromaticity of the test piece was determined with a colorimeter (manufactured by Nippon Denshoku Industries Co., Ltd. under the product number Model Σ90, C light source, field of color detected: 2°). The degree of discoloration was obtained by comparing the chromaticity before the immersion of the test piece with the chromaticity after the immersion, and the difference of each of chromaticities was expressed as $\Delta E^*$. The larger the numerical value of $\Delta E^*$ meaning the larger the coloration, and the poorer the anti-staining property.

[Discoloration Test of Cured Product]

In order to evaluate the discoloration property of the cured coating agent itself, the following test was conducted. As a substrate to which the coating agent was applied, a 20 mm×15 mm glass plate having a thickness of 1 mm was selected, and one side of the glass plate is subjected to a sand-blast treatment with alumina, and further applied with a 0.2% ethanol solution of a silane coupling agent (3-methacryloyloxypropyltrimethoxysilane) as a primer.

A photopolymeric coating solution was applied to the glass surface with a brush, and allowed to stand at room temperature for 10 minutes. Thereafter, the glass surface was further mildly air-blown to evaporate the solvent ethanol. The photopolymeric coating was subjected to photoirradiation with a dental photoirradiator (manufactured by Kulzer under the trade name of UNIXS) for 90 seconds to polymerize and cure the photopolymeric coating, whereby a coating film having anti-staining property, in which an unpolymerized layer was not remaining on the surface was formed. Here, the thickness of the coating agent layer was adjusted to be 200 μm with a spacer and a mold-releasing film (EVAL) before the photoirradiation.

The test plate obtained was stored in water at 70° C. for 7 days, and the chromaticities before and after the immersion were compared, thereby evaluating the degree of discoloration. In the same manner as that previously mentioned, the chromaticity of the test piece before the immersion and the chromaticity of the test piece after the immersion were compared, and the difference of each of the chromaticities was expressed as ΔE*. The larger the numerical value of ΔE* meaning the larger the discoloration of the cured product.

[Abrasion Resistance Test]

A toothbrush wear test was conducted using as a test piece a product obtained by applying and curing a coating agent on the above-mentioned bovine teeth enamel.

A commercially available toothpaste [manufactured by Lion Corporation under the trade name of Dentor T] and water were mixed so as to have a ratio of toothpaste/water (weight ratio) of 60/40. A test piece was placed in the suspension obtained, and rubbed over the coated layer by reciprocating 10,000 times with a toothbrush to which a 200 g load was applied to cause abrasion. The surface roughness of the surface subjected to abrasion was determined with a surface roughness gauge [manufactured by K.K. Kosaka Seisakusho under the product number of Model SE-3C], and states before and after the abrasion were compared, and whereby a depth (abrasion depth) subjected to abrasion with the toothbrush was calculated.

Synthesis Example 1

Synthesis of Fluorine Compound

To a solution (50 g) composed of acrylic acid (49 mmol, 3.6 g) and a mixed solvent of $CF_3CF_2CHCl_2$ and $CHFClCF_2CF_2Cl$ [manufactured by ASAHI GLASS CO., LTD. under the product number of AK-225] (a mixed solvent in which a volume ratio of $CF_3CF_2CHCl_2$ to $CHFClCF_2CF_2Cl$ is 1:1) was added 70 g of a solution prepared by adding perfluoro-2,5-dimethyl-3,6-dioxanonanoyl peroxide (5 mmol, 4.9 g) to the mixture solvent AK-225, and the mixture was reacted at 45° C. under nitrogen gas stream for 5 hours.

After the termination of the reaction, the resulting white powder was subjected to suction filtration, and the product was further sufficiently washed with hexane to be purified. Further, the product obtained was dried at 50° C. in vacuo for 2 days. As a result, a desired product, a polyacrylic acid blocked with fluoroalkyl groups at both ends, was obtained in an yield of 4.7 g. The spectra of the resulting product are as follows.

[Rf—$(CH_2CHCOOH)_g$—Rf], wherein g is a degree of polymerization [Rf—$CF(CF_3)OCF_2CF(CF_3)OC_3F_7$]

number-average molecular weight (determined by gel permeation chromatography, eluate:tetrahydrofuran): 4250 infrared absorption spectrum ν ($cm^{-1}$): 3200 (OH), 20 (C=O), 335 ($CF_3$), 240 ($CF_2$)

$^1$H-NMR ($CD_3OD$) δ: 1.35-2.19 ($CH_2$), 2.21-2.72 (CH)

Example 1

A photo-curable coating composition having the following composition was prepared. Specifically, 35 parts by weight of dipentaerythritol hexacrylate [manufactured by Kyoei Kagaku Kogyo K.K. under the trade name of DPE-6A, hereinafter referred to as "DPA6"] as a polymerizable monomer, 15 parts by weight of methyl methacrylate (hereinafter referred to as "MMA"), and 1 part by weight of 2,4,6-trimethylbenzoyl diphenylphosphine oxide (hereinafter referred to as "TMDPO") as a photopolymerization initiator were homogeneously dissolved.

As a fluorine compound (a), 0.5 parts by weight of the compound of a polyacrylic acid having perfluoroalkyl groups at both ends obtained in Synthesis Example 1 (hereinafter referred to as "ACA") was mixed with 50 parts by weight of a solvent ethanol (99%) to be homogeneously dissolved therein.

Fifty parts by weight of the above-mentioned polymerizable monomer solution and 50 parts by weight of the ethanol solution in which a fluorine compound was dissolved were mixed to produce a homogeneous solution, to give a polymerizable composition of the present invention. This polymerizable composition was subjected to the anti-staining property test, the discoloration test, and the abrasion resistance test. The results are shown in Table 1.

Examples 2 to 13 and Comparative Examples 1 to 6

A photopolymerizable coating agent was prepared in the same manner as in Example 1 using a fluorine compound or polymer listed in Table 1 in place of the ACA in Example 1, and its physical properties were evaluated. The results are shown in Tables 1 and 2.

TABLE 1

| No. | Fluorine Compound or Polymer | | Anti-Staining Property (ΔE*) | Discoloration (ΔE*) | Abrasion Depth (μm) |
|---|---|---|---|---|---|
| Ex. 1 | Rf—$(CH_2$—$CH)_n$—Rf<br>         $\|$<br>       COOH | (Mn = 4250) | 10.2 | 1.9 | 11 |
| Ex. 2 | Rf—$(CH_2$—$CH)_n$—Rf<br>         $\|$<br>     $CON(CH_3)_2$ | (Mn = 8700) | 32.7 | 2.4 | 13 |
| Ex. 3 | Rf—$(CH_2$—$CH)_n$—Rf<br>         $\|$<br>     $COO(CH_2)_2$—OH | (Mn = 1100) | 27.9 | 2.0 | 16 |

TABLE 1-continued

| No. | Fluorine Compound or Polymer | | Anti-Staining Property ($\Delta E^*$) | Discoloration ($\Delta E^*$) | Abrasion Depth ($\mu m$) |
|---|---|---|---|---|---|
| Ex. 4 | Rf—(CH$_2$—CH)$_n$—Rf<br>        \|<br>        COO(CH$_2$)$_2$—O—P(O)(OH)$_2$ | (Mn = 13300) | 15.9 | 1.5 | 9 |
| Ex. 5 | Rf—(CH$_2$—CH)$_n$—Rf<br>        \|<br>        CON$^+$H$_2$—C(CH$_3$)$_2$(CH$_2$)—SO$_3^-$ | (Mn = 12000) | 12.4 | 2.1 | 14 |
| Ex. 6 | Rf—(CH$_2$—CH)$_n$—(CH$_2$—C(CH$_3$))$_m$—Rf<br>        \|                \|<br>        COOH       COOCH$_3$ | (n/m = 85/15, Mn = 8900) | 18.0 | 3.3 | 18 |
| Comp. Ex. 1 | None | | 70.3 | 2.1 | 13 |
| Comp. Ex. 2 | Polyacrylic acid (molecular weight: 20000) (not containing fluorine atom) | | 68.3 | 4.1 | 29 |
| Comp. Ex. 3 | Rf—(CH$_2$—CH)$_n$—Rf<br>        \|<br>        COO(CH$_2$)$_3$—Si(OCH$_3$)$_3$ | (Mn = 9700) | 60.7 | 7.9 | 45 |
| Comp. Ex. 4 | Random Copolymer of 8FMA (1H,1H,5H-Octafluoropentyl methacrylate) and Acrylic acid in a molar ratio of 1:20 | (Mn = 15700) | 67.4 | 3.5 | 19 |

(Note)
Rf: —CF(CF$_3$)—OCF$_2$CF(CF$_3$)—OC$_3$F$_7$
Mn: Number-average molecular weight

TABLE 2

| No. | Fluorine Compound or Polymer | | Anti-Staining Property ($\Delta E^*$) | Discoloration ($\Delta E^*$) | Abrasion Resistance ($\mu m$) |
|---|---|---|---|---|---|
| Ex. 7 | Rf—(CH$_2$—CH)n—(CH$_2$—C(CH$_3$))m—Rf<br>      \|                \|<br>      COOH     COO—(CH$_2$)$_{10}$—OP(O)(OH)$_2$ | (n:m = 4:1, Mn = 6700) | 16.1 | 0.9 | 8 |
| Ex. 8 | Rf—(CH$_2$—CH)n—(CH$_2$—C(CH$_3$))m—Rf<br>      \|                \|<br>      COOH     COO—(CH$_2$)$_2$—OP(O)(OH)$_2$ | (n:m = 2:1, Mn = 3800) | 11.7 | 1.5 | 15 |
| Ex. 9 | Rf—(CH$_2$—C(CH$_3$))n—Rf<br>      \|<br>      COO—(CH$_2$)$_{10}$—OP(O)(OH)$_2$ | (Mn = 3100) | 20.1 | 1.1 | 11 |
| Ex. 10 | Rf—(CH$_2$—C(CH$_3$))n—Rf<br>      \|<br>      COO—(CH$_2$)$_2$—N(CH$_3$)$_3^+$Cl$^-$ | (Mn = 2900) | 13.0 | 2.2 | 19 |
| Ex. 11 | Rf—(CH$_2$—CH)n—(CH$_2$—C(CH$_3$))m—Rf<br>      \|                \|<br>      COOH     COO—(CH$_2$)$_{12}$—Rpy | (n:m = 5:1, Mn = 5700) | 19.4 | 2.3 | 13 |
| Ex. 12 | Rf—(CH$_2$—C(CH$_3$))n—Rf<br>      \|<br>      COO—(CH$_2$)$_2$—COOH | (Mn = 4900) | 16.3 | 0.8 | 9 |
| Ex. 13 | Rf—(CH$_2$—CH)n—(CH$_2$—C(CH$_3$))m—(CH$_2$—C(CH$_3$))l—Rf<br>      \|              \|                \|<br>      COOH   COO(C$_2$H$_4$O)$_4$H   COO(CH$_2$)$_{10}$—OP(O)(OH)$_2$ | (n:m:l = 4:1:1, Mn = 9700) | 18.7 | 1.6 | 10 |
| Comp. Ex. 5 | Rf—(CH$_2$—CH)n—(CH$_2$—C(CH$_3$))m—Rf<br>      \|                \|<br>      Si(OCH$_3$)$_3$   COOCH$_3$ | (n:m = 1:5, Mn = 3400) | 56.8 | 3.6 | 23 |

TABLE 2-continued

| | | | | |
|---|---|---|---|---|
| Comp. Ex. 6 | Rf—(CH$_2$—C(CH$_3$))n—Rf<br>                  \|<br>                  COO(CH$_2$)$_{11}$CH$_3$ | (Mn = 11000) | 70.4 | 2.0 | 20 |

(Note)

Rpy: 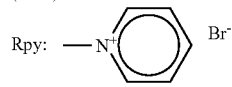

It can be seen from the results shown in Tables 1 and 2 that when Example 1 is compared with Comparative Examples 1 and 2, the anti-staining property is dramatically improved by using a compound in which groups containing a fluoroalkyl group are introduced into both ends of the main chain of the polyacrylic acid. In addition, Comparative Example 4 has a structure in which fluoroalkyl groups are randomly introduced into the main chain of the polyacrylic acid; however, there are hardly any effects in the anti-staining property in the dental applications, so that it can be seen that it is important to use a polymer having fluoroalkyl groups at both ends.

It can be seen in Comparative Example 3 where the polymer does not contain any monomer units containing a hydrophilic group that the effect on the anti-staining property is not exhibited in dental applications. In addition, as compared to Comparative Example 3, it can be seen that the polymerizable composition obtained in each example is excellent in discoloration of the cured product and abrasion resistance.

Examples 14 to 18

A polymerizable composition was prepared in the same manner as in Example 1 except that the amount of ACA was changed to that listed in Table 3 in the coating agent of Example 1, and the chromaticity (anti-staining property) was determined. The results are shown in Table 3.

TABLE 3

| No. | Amount of ACA (Parts by Weight) | Chromaticity (ΔE*) |
|---|---|---|
| Comp. Ex. 1 | 0 | 70.3 |
| Ex. 14 | 0.05 | 23.7 |
| Ex. 15 | 0.1 | 11.5 |
| Ex. 16 | 0.2 | 9.8 |
| Ex. 1 | 0.5 | 10.2 |
| Ex. 17 | 1 | 9.1 |
| Ex. 18 | 2 | 13.1 |

It can be seen from the results shown in Table 3 that the coloration can be controlled at a low level in a case where the content of the fluorine compound is 0.1 parts by weight or more, based on 100 parts by weight of the polymerizable monomer, and that the coloration is controlled at an even lower level in a case where the content of the fluorine compound is 0.2 parts by weight or more.

Reference Example 1

A test piece for an anti-staining property test coated in the same manner as in Example 1 using the polymerizable composition of Example 1 was prepared. The test piece for an anti-staining property test was immersed in 70% ethanol and stirred for 30 minutes, to wash the coated surface.

After washing, the test piece was subjected to a coloration test (anti-staining property test) with turmeric in the same manner as in Example 1. As a result, the value for ΔE* was 11.5, so that the anti-staining property was not substantially impaired by washing.

Reference Example 2

A test piece for an anti-staining property test coated in the same manner as in Example 1 using the polymerizable composition of Example 1 was prepared. The test piece for an anti-staining property test was immersed in water at 37° C. for 10 days, and thereafter subjected to a coloration test (anti-staining property test) with turmeric in the same manner. As a result, the value for ΔE* was 10.6, so that the anti-staining property of the surface was not substantially impaired by immersion in water for a long period of time.

Reference Example 3

A test piece for an anti-staining property test prepared by coating in the same manner as in Example 1 using the polymerizable composition of Example 1 was immersed in a saturated aqueous calcium hydroxide solution at 25° C. for 5 minutes. The test piece was subjected to a coloration test (anti-staining property test) with turmeric in the same manner. As a result, the value for ΔE* was 8.5, thereby showing an excellent anti-staining property.

Reference Example 4

Adhesion Test for Plaque

A coated test piece was placed in an artificial oral cavity device, and the adhesion of plaque was evaluated by quantifying the amount of biofilm (plaque) adhered to the surface.

The details of the artificial oral cavity device and the test conditions employed herein were in accordance with those described in *Journal of Dental Research*, 83 (2004) Special Edition A, Abstract No. 209, and *Nippon Shika Giko Gakkai Zasshi (Japan Academy Dental Technology)* 25(2) (2004), 242.

Specifically, a coating agent used in Example 1 was applied on a rigid resin cured plate for crown and inlay, and the coated plate was photo-cured, thereby forming a coated surface. The coating agent was tested for plaque adhesion. In other words, a paste of a commercial rigid resin for crown and inlay [manufactured by Kuraray Medical Inc. under the trade name of Estenia C & B (E1 Shade)] was injected into a mold having a hole opening of 4 mm×4 mm×1.5 mm, and pressed with a glass plate. The photopolymerization (3 minutes) was carried out with a dental photoirradiation device (manufactured by J. MORITA TOKYO MFG. CORP. under the trade name of Alpha-Light II), and thereafter a heat treatment (at 110° C. for 15 minutes) was carried out with a dental heating device [manufactured by Kuraray Medical Inc. under the product number of KL100], to prepare a test plate having dimensions of 4 mm×4 mm×1.5 mm.

Next, the surface of the test plate was ground with a silicon carbide paper (#800), and the photopolymerizable coating agent obtained in Example 1 was taken in an amount of 0.5 µ/L with a micropipette and applied to a surface of the ground test plate, and the solvent was slowly evaporated and dissipated. Thereafter, the photopolymerization (3 minutes) was carried out with a photoirradiation device (manufactured by Morita under the trade name of Alpha-Light II), to prepare a coated surface, and the surface was used as a test surface.

The above-mentioned sample was fixed in a holder made of a fluororesin placed inside the artificial oral cavity device using utility wax. This device is a test device capable of artificially forming a biofilm (plaque) on a test surface by continuing to add dropwise a solution containing bacteria in the oral cavity and a culture medium, the atmosphere therein being kept at 37° C., to a test surface for a long period of time, and thereby providing a test surface with an environment similar to that inside the oral cavity. Specific test procedures are as follows.

Previously collected saliva was centrifuged (rotational speed: 15,000 rpm), and the supernatant was filtered using a filter (0.22 µm CA). This filtrate was poured on the test surface of the sample, and allowed to stand for 30 minutes, to allow the formation of pellicle on the test surface.

As solutions to be added dropwise to this test surface, three solutions, i.e. a bacterial suspension obtained by using *Streptococcus mutans* MT8148 as a bacterium, culturing the bacterium in a BHI liquid medium, collecting the bacterium, washing the bacterium with PBS (phosphate-buffered physiological saline), and thereafter re-suspending the bacterium in the same buffer at $OD_{500}=2$ (about $2 \times 10^7$ CFU/mL), a medium HI (Heart Infusion Broth, containing 1% sucrose as a saccharide), and PBS were continuously added dropwise from each tube.

Here, the dropwise addition was continued for 20 hours, while continuously recording the pH with a planar pH electrode placed inside the holder made of a fluororesin. With the formation of the artificial plaque, the dropwise addition was terminated when the pH was lowered to a level near 4.0.

After the dropwise addition, the test sample was taken out, and placed in a test tube containing PBS, and vibration was applied thereto for 15 seconds using a vibrator (Vortex-2 Genine/Level 5, manufactured by Scientific Industry Inc., N.Y., USA). Plaque remaining on the surface without being removed from the test surface of the sample was quantified. Specifically, a test plate to which plaque was adhered was treated with a 0.5 N aqueous sodium hydroxide solution, and thereafter treated solution was centrifuged (rotational speed: 3000 rpm), to separate into precipitates and supernatant. The precipitates were re-dispersed in PBS, and turbidity ($OD_{500}$) of the precipitates was determined with a spectrophotometer, and defined as the amount of the bacterium. In addition, the supernatant was quantified by phenol sulfate analysis method, and determined with a spectrophotometer, to quantify a non-water-soluble glucan. The larger the turbidity and the amount of the non-water-soluble glucan, the larger the amount of plaque adhered. The results are shown in Table 4, wherein the numerical values listed in Table 4 are an average of the values obtained from 3 sample plates.

Comparative Reference Example 1

The adhesion test of plaque was carried out in the same manner as in Reference Example 4 except that the coating agent of Comparative Example 1 not containing a fluorine oligomer was used as a coating agent in Reference Example 4, and plaque remaining on the surface was quantified. The results are shown in Table 4.

TABLE 4

|  | Turbidity (S.D.) | Non-Water-Soluble Glucan (S.D.) |
| --- | --- | --- |
| Ref. Ex. 4 | 0.064 (0.008) | 12.2 (6.9) µg/mL |
| Comp. Ref. Ex. 1 | 0.104 (0.023) | 21.7 (11.4) µg/mL |

It can be seen from the results shown in Table 4 that the polymerizable composition of Example 1 used in Reference Example 4 has a smaller amount of plaque remaining on the surface, as compared to that of the polymerizable composition of Comparative Example 1 used in Comparative Reference Example 1. Here, it is suggested from the results that the polymerizable composition which gives excellent evaluation in the above-mentioned anti-staining property test using the turmeric pigment is also excellent in the inhibition of the adhesion of plaque.

Reference Example 5

The following evaluation for the anti-staining property was made using the coating agent of Example 1 in the same manner as in the above-mentioned anti-staining property test except that the same substrate [cured product of crowning rigid resin (Estenia C & B)] as in Reference Example 4 was used in place of the bovine teeth, and that an etching treatment was not carried out.

The anti-staining property of the coated surface was evaluated with a turmeric suspension in the same manner as in Example 1 using a test piece obtained by coating the above-mentioned substrate with the coating agent of Example 1. As a result, $\Delta E^*$ was 9.5, showing excellent anti-staining property.

Comparative Reference Example 2

A composition excluding the polymerizable monomer and the polymerization catalyst from the coating agent of Example 1 (a composition prepared by mixing 50 parts by weight of ethanol and 0.5 parts by weight of the fluorine compound used in Example 1 (ACA), to homogeneously dissolve) was prepared. This composition was applied as a coating agent with a brush to a cured surface of the above-mentioned substrate (crowning rigid resin), and allowed to stand at room temperature for 2 hours to remove the solvent, thereby coating the surface of the substrate with a fluorine compound. This test piece was immersed in a turmeric suspension in the same manner as in Reference Example 5 to evaluate the anti-staining property. As a result, $\Delta E^*$ was 30.8.

In Comparative Reference 2, it is presumed that the effect on the anti-staining property was not obtained because the fluorine compound was removed from the substrate. On the other hand, in Reference Example 5, it is considered that an excellent effect on the anti-staining property was obtained because a polymerizable monomer was contained and a fluorine compound was immobilized by a coating film obtained by polymerizing and curing the polymerizable monomer.

INDUSTRIAL APPLICABILITY

The dental polymerizable composition of the present invention can be suitably used, for example, for dental composite resins, such as dental composite filler materials, crowning materials, and bonding materials; dental adhesive agents, such as teeth-straightening adhesive agents, cavity-coating adhesive agents, and tooth fissure sealing materials; denture base materials, denture base mucosal adjusting materials, fissure sealants, coating agents applied to tooth surface or dental prosthetic, surface glazes, and the like, and especially for various coating applications, for example, a fissure sealant, a coating agent to tooth surface or dental prosthetic, surface stains or a surface glaze, a hypersensitive inhibitor, a dental manicure, or the like.

The invention claimed is:

1. A dental polymerizable composition comprising:
   (a) a fluorine compound;
   (b) a polymerizable monomer; and
   (c) a polymerization initiator,
   wherein the fluorine compound is a chain polymer having a main chain comprising a monomer unit having a hydrophilic group, and terminal groups comprising a fluoroalkyl group at each of both ends of the main chain, the chain polymer having a number-average molecular weight of from 1,000 to 100,000, the main chain optionally comprising a unit other than the monomer unit having a hydrophilic group in a ratio of 50% by mol or less of the entire monomer units.

2. The dental polymerizable composition according to claim 1, wherein the fluorine compound is contained in an amount of from 0.001 to 30 parts by weight, based on 100 parts by weight of the polymerizable monomer.

3. The dental polymerizable composition according to claim 1 or 2, wherein the hydrophilic group is at least one hydrophilic group selected from the group consisting of an acidic group or a salt thereof, a quaternary ammonium salt group, and an amphoteric ionic group.

4. The dental polymerizable composition according to claim 1 or 2, wherein the hydrophilic group is at least one hydrophilic group selected from the group consisting of a carboxylic acid group or a salt thereof, a phosphoric acid group or a salt thereof, a phosphonic acid group or a salt thereof, a sulfonic acid group or a salt thereof, a trimethylammonium chloride group, a pyridinium chloride group, a pyridinium bromide group, an alkylbetaine group, a carboxybetaine group, a sulfobetaine group, and a phosphobetaine group.

5. The dental polymerizable composition according to claim 1 or 2, wherein the main chain comprises a unit other than the monomer unit having a hydrophilic group in a ratio of 50% by mol or less of the entire monomer units.

6. The dental polymerizable composition according to claim 1 or 2, wherein the polymerization initiator is a photopolymerization initiator that is excited with light at a wavelength of from 350 to 700 nm.

7. The dental polymerizable composition according to claim 1 or 2, further comprising (d) a solvent.

8. The dental polymerizable composition according to claim 7, wherein the fluorine compound is contained in an amount of from 0.001 to 30 parts by weight, the polymerization initiator is contained in an amount of from 0.05 to 10 parts by weight, and the solvent is contained in an amount of from 30 to 1000 parts by weight, each based on 100 parts by weight of the polymerizable monomer.

9. A single-liquid dental coating agent comprising the dental polymerizable composition as defined in claim 1 or 2 in a single wrapping.

10. A method for curing a dental polymerizable composition, comprising applying the dental polymerizable composition as defined in claim 7 to surfaces of teeth or a dental restorative material, allowing a solvent contained in the dental polymerizable composition to evaporate, and curing the residue, thereby forming a layer comprising a fluorine compound on the surfaces of the teeth or the dental restorative material.

* * * * *